United States Patent [19]

Austin et al.

[11] Patent Number: 5,222,948
[45] Date of Patent: Jun. 29, 1993

[54] INJECTION PORT FOR SINGLE-USE SYRINGE

[75] Inventors: Glenn Austin, Seattle; Carib Nelson, Bellevue; Ronny D. Thomas, Freeland, all of Wash.

[73] Assignee: Path, Seattle, Wash.

[21] Appl. No.: 756,889

[22] Filed: Sep. 9, 1991

[51] Int. Cl.$^5$ .................................... A61M 5/178
[52] U.S. Cl. ............................ 604/213; 604/200; 604/240; 604/246; 604/905; 137/855
[58] Field of Search ............... 604/200, 201, 212, 213, 604/215-217, 240, 243, 244, 246, 247, 905; 137/855

[56] References Cited

U.S. PATENT DOCUMENTS

| | | | |
|---|---|---|---|
| 1,668,588 | 5/1928 | Greeley | 604/201 X |
| 2,232,978 | 2/1941 | Smith | 604/201 X |
| 2,460,039 | 1/1949 | Scherer et al. | 604/201 X |
| 2,607,344 | 8/1952 | Brown | 604/201 X |
| 2,768,623 | 10/1956 | Marchland | 604/212 X |
| 3,021,841 | 2/1962 | Burke . | |
| 3,065,761 | 11/1962 | Péras | 137/855 X |
| 3,664,339 | 5/1972 | Santomieri . | |
| 3,667,657 | 6/1972 | Chiquiar-Arias . | |
| 3,890,971 | 6/1975 | Lesson et al. . | |
| 3,951,146 | 4/1976 | Chiquiar-Arias . | |
| 3,955,648 | 5/1976 | Walker et al. | 137/855 X |
| 3,998,224 | 12/1976 | Chiquiar-Arias . | |
| 4,020,836 | 5/1977 | Cunnigham | 604/201 |
| 4,111,228 | 9/1978 | Simionescy | 137/512 |
| 4,222,407 | 9/1980 | Ruschke et al. | 137/512.15 |
| 4,233,975 | 11/1980 | Yerman . | |
| 4,331,146 | 5/1982 | Brignola | 604/200 |
| 4,349,035 | 9/1982 | Thomas et al. | 128/766 |
| 4,666,429 | 5/1987 | Stone | 604/83 |
| 4,776,848 | 10/1988 | Solazzo | 604/247 |
| 4,883,473 | 11/1989 | Thomas | 604/217 |
| 4,936,830 | 6/1990 | Verlier . | |
| 4,941,879 | 7/1990 | Butler et al. . | |
| 4,952,206 | 8/1990 | Ibanez et al. . | |
| 4,955,871 | 9/1990 | Thomas | 604/217 |
| 5,062,779 | 11/1991 | Da Costa | 418/270 |
| 5,137,522 | 8/1992 | Bron | 604/247 |
| 5,176,658 | 1/1993 | Ranford | 604/247 |

FOREIGN PATENT DOCUMENTS

| | | | |
|---|---|---|---|
| 0971453 | 7/1975 | Canada | 604/200 |
| 2723142 | 11/1978 | Fed. Rep. of Germany | 604/212 |
| 2573310 | 5/1986 | France | 604/212 |
| 0789926 | 1/1958 | United Kingdom | 604/200 |

*Primary Examiner*—John D. Yasko
*Assistant Examiner*—Mark O. Polutta
*Attorney, Agent, or Firm*—Wegner, Cantor, Mueller & Player

[57] ABSTRACT

An improved injection port (1) for a single-use syringe is described. One embodiment of the injection port has a one-way valve system for making it more difficult to reuse the syringe (2). The one-way valve system has a flap or diaphragm valve (6) housed in a valve chamber (11) at the proximal end of port cylinder (45). When the valve (6) is seated against valve seat (51) on valve cap (5), refilling of the syringe is blocked. During injection, the valve (6) unseats and moves toward radial ribs (7), allowing flow of medicament into the proximal end of a needle (2). Another embodiment of the injection port (1) includes longitudinal grooves (8) on the interior surface of the chamber (12) at the distal end of cylinder (45). The grooves (8) vent pressure from a Luer syringe inserted in the distal end of the cylinder (45).

18 Claims, 5 Drawing Sheets

INJECTION PORT FOR SINGLE-USE SYRINGE

FEDERALLY-SPONSORED RESEARCH AND DEVELOPMENT

The U.S. Government has contributed support to this invention under Federal Grant Number DPE-5968-A-00-0025-00 awarded by the Agency for International Development. The U.S. Government has certain rights in the invention.

BACKGROUND OF THE INVENTION

This invention relates to improvements in an injection port structure for use with syringes, to manufacture of syringes with the improved injection port, and more particularly to improved means for preventing reuse of syringes.

The rapid spread of acquired immune deficiency syndrome (AIDS) among intravenous drug users has created an urgent need for syringes that cannot be reused. In many situations, injections are given to patients without carefully controlling access to syringes. The use of reusable syringes under those circumstances increases the risk of infection. An infection can occur whenever syringes that have been used previously, and which therefore are no longer sterile, are used to administer injections.

Of course, reusable syringes are suitable for administration of a vaccine or other injectable medicaments when the injections are performed by a professional staff in formal health care facilities. In a hospital environment, skilled personnel sterilize the syringe for reuse, refill the syringe with the appropriate medicament, and personally administer the injections. Furthermore, circulation of these syringes is managed and controlled.

However, there are times when it is necessary or more economical to administer injections outside a hospital environment. For example, it may be necessary to give injections to a large number of individuals over a short period of time, patients may be located in a developing country or in an area without convenient access to a hospital or medical personnel, or it may be desirable to permit injections to be administered to a patient at his or her home or while he or she travels. Under these circumstances, it is very difficult to prevent misuse of the syringes. Furthermore, it is difficult to ensure proper sterilization of the syringes, particularly if medicaments are administered by non-professional personnel.

It is also important to develop an easy method of manufacturing a syringe having means for effectively preventing reuse of the syringe. Even though the use of disposable syringes reduces the risk of infection, it is not economically feasible to replace reusable syringes with disposable syringes unless the disposable syringes are made in a relatively inexpensive manner.

In view of the need for non-reusable syringes, various designs have been developed. For example, U.S. Pat. No. 3,667,657 describes a syringe having a knife which cuts the syringe wall to prevent reuse, while U.S. Pat. Nos. 3,951,146 and 3,998,224 disclose similar self-destructing syringe systems. A single-use syringe as described in U.S. Pat. No. 3,890,971 includes permanently-lockable plunger and slidable needle cap mechanisms.

Additionally, various valve designs have been developed for use with different syringe systems. For instance, U.S. Pat. No. 4,936,830 discloses a prefilled syringe having a one-way ball valve which only allows communication of the compartment containing the substance to be injected with the needle during injection. U.S. Pat. No. 4,952,206 describes another single-use syringe having an expandable plug which expands to engage a conical washer against an opening to prevent flow.

However, single-use syringes that have been developed suffer from various drawbacks, such as being expensive to manufacture, or being so bulky that the syringes are inconvenient to ship and store. Moreover, some known syringe designs are difficult to aspirate.

In order to ensure proper administration of an injection, it is important that the syringe be designed to allow aspiration to verify proper placement of the needle in the patient. Trained medical personnel confirm whether a needle is or is not in a blood vessel by aspirating prior to injection of a medicament. In aspiration, a negative or suction pressure causes the needle to draw material into the syringe from the patient. The person administering the injection then visually examines the syringe to see if any blood has been drawn into the syringe through the needle. If, for example, the injection should be administered intravenously, the presence of blood after aspiration indicates proper placement of the needle.

It is difficult to design a single-use syringe accommodating aspiration. Disposable syringes that contain a prefilled vaccine delivery system typically have a squeezable body portion or other elastic receptacle. In these syringes, a positive pressure is applied on or by the receptacle to force the medicament out through the needle. In order to perform aspiration, however, a negative pressure is applied to the receptacle. Unfortunately, the negative pressure needed to aspirate the syringe also may be used to reform the elastic receptacle, allowing the syringe to be reused.

In view of the need for an inexpensive and easy way to manufacture syringes that are difficult to reuse, but which can be used to perform aspiration, a syringe was developed as described in U.S. Pat. No. 4,955,871 to Thomas, the disclosure of which is hereby incorporated by reference. The Thomas syringe is provided with a reservoir for storing medicament and expelling it into the needle. The reservoir of the Thomas syringe provides for an "oil-can type" of flexing action.

In the Thomas syringe, the reservoir is formed by two sheets of thermoplastic material having expanded central portions forming a pair of compressible, convex domes. A connecting member spaces apart the domes. In response to complete compression of both of the central portions together, the reservoir substantially collapses and each of the domes becomes concave. This oil-can type action prevents the reservoir from being reformed and makes it difficult to reuse the syringe. However, after partial compression of the central portions together and partial collapse of the reservoir, upon removal of the compressing force the central portions expand to reform the reservoir and draw fluid into the reservoir, thereby aspirating a hypodermic needle.

It has now been found that the Thomas syringe can be reused with difficulty by one of two techniques. First, the oil-can action of the reservoir of the Thomas syringe can be overcome by inserting the needle of a used Thomas syringe into a pressurized container of the desired injectable material, whereupon the pressure blows the reservoir walls apart and fills it with the desired material for injection. Second, the Thomas syringe can be reused by putting the desired material into a Luer syringe, removing the needle from a used Thomas syringe, inserting the tip of the Luer syringe into the nozzle or port cylinder of the Thomas syringe, and injecting the desired material.

SUMMARY OF THE INVENTION

In view of the above-mentioned drawbacks of known syringe designs, an object of this invention is to provide an improved port cylinder for a Thomas syringe or similar device which makes the syringe more difficult to reuse.

Another object is to provide a means for making a conventional syringe more difficult to reuse at little additional manufacturing cost.

An additional object of the present invention is to help prevent reuse of a Thomas or like syringe by either or both of the two aforementioned techniques for overcoming the flexing action of the reservoir.

According to a preferred embodiment of the invention, a syringe device comprises an improved injection port having a one-way valve means. In this embodiment, an injection port having a diaphragm valve is provided for use in a medical syringe to permit substantial fluid flow toward the distal end of the syringe and prevent substantial fluid flow toward the proximal end of the syringe. The injection port assembly is adapted to be positioned in a syringe between a medicament reservoir and a hypodermic needle and comprises a cylindrical valve chamber forming a fluid-tight seal with the syringe, the distal wall of the valve chamber having a central aperture adapted to make a secure fluid connection with the hypodermic needle. A plurality of radial ribs surrounds the central aperture and extends from the aperture to the outer circumferential wall of the chamber thereby defining both a central passage extending in a proximal direction and a series of passages between the ribs, the passages communicating with the central passage. A valve seat closes the proximal end of the valve chamber and has a central aperture connecting the chamber with the medicament reservoir, with a valve flap disposed in the chamber between the valve seat and the ribs. The valve flap is free to move between the valve seat surface and the ribs as pressure is applied to the valve flap by fluid entering the valve chamber from the apertures at each end of the chamber. The valve flap has a diameter smaller than the interior diameter of the chamber, but large enough to seal the proximal aperture while in contact with the circumferential wall of the chamber when fluid seeks to move into the reservoir and also large enough to cover the central passage at the distal end of the chamber but not all of the passages between the ribs when fluid moves from the reservoir toward the distal end. The valve flap may be hinged on one side, but preferably is free floating.

A syringe device according to another embodiment of the invention has vent means for venting the elongated chamber of the injection port to the atmosphere.

Additionally, the invention involves the combination of the one-way valve means and the vent means in combination in an improved injection port.

The invention also relates to an improved syringe device comprising any of the above injection ports in combination with a needle assembly, reservoir, and protector cap.

In addition to the above, additional objects and embodiments of the invention will be apparent from the detailed description with reference to the accompanying drawings.

BRIEF DESCRIPTION OF THE DRAWINGS

FIG. 1b is an axial view of the injection port taken from the distal end of the injection port of FIG. 1a. FIG. 1c is an axial view of the injection port taken from the proximal end of the injection port of FIG. 1a.

FIG. 2b is an axial view of the valve seat taken from the distal end of valve seat of FIG. 2a.

FIG. 3a is a side cross-sectional view of a needle hub used in combination with the injection port of FIG. 1a. FIG. 3b is an axial view of the needle hub taken from the distal end of the needle hub of FIG. 3a.

FIG. 4b is an axial view of the needle cap taken from the distal end of the needle cap of FIG. 4a.

DESCRIPTION OF PREFERRED EMBODIMENTS

In FIGS. 1a-1e, an injection port 1 is shown having a port cylinder or tubular wall 45 which, in turn, has an interior wall surface 45a and an exterior wall surface 45b. The port cylinder 45 is divided by a membrane 42 into an elongated chamber 12 and a valve chamber 11. Wall 45 has an exterior circumferential flange 4 which assures accurate positioning of the port 1 in relation to medicament reservoir 102b (see FIG. 5) during assembly of the syringe and assists in activation as described hereinafter. The elongated chamber 12 has a proximal chamber end 12' and a distal chamber end 12". Circumferential ribs or lips 9 may be provided on the interior wall surface 45a of the port cylinder 45 to hold the needle hub 3 in place prior to activation as described hereinafter.

Figure 3A:
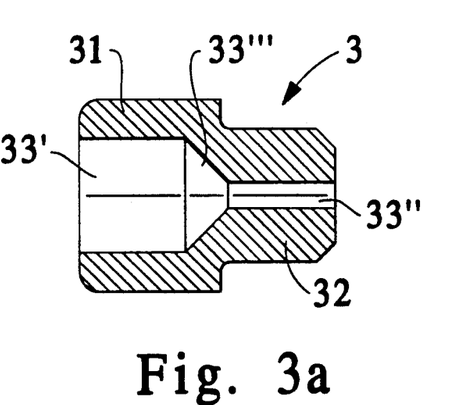
Figure 3B:
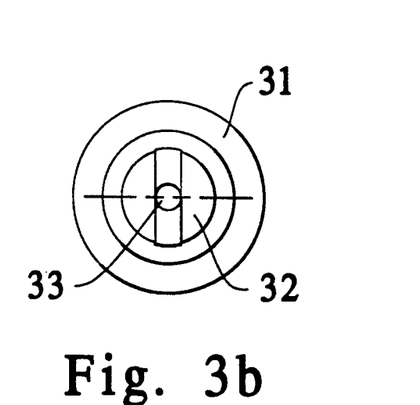
Figure 3C:
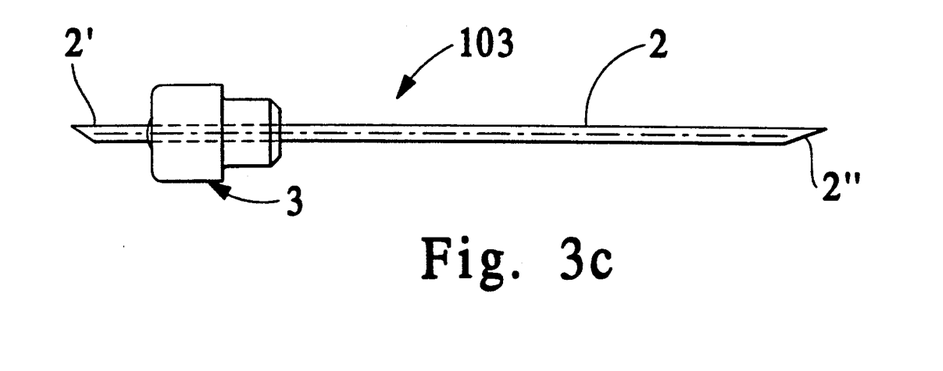
FIG. 3c is a side view of the needle hub of FIG. 3a with the needle assembled therein.
Figure 4A:
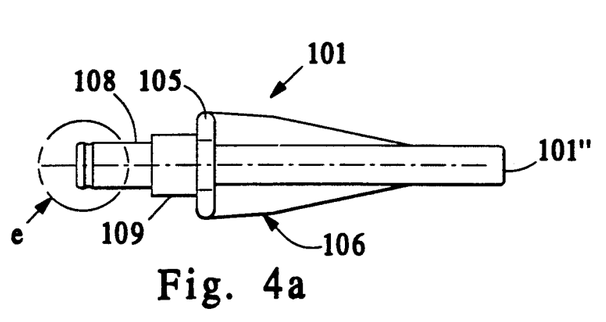
FIG. 4a is a side view of the needle cap used in combination with the injection port of FIG. 1a and the needle hub assembly of FIG. 3c.
Figure 4B:
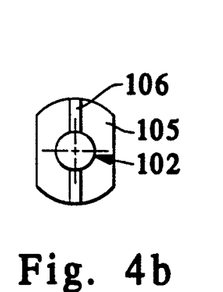
Figure 4C:
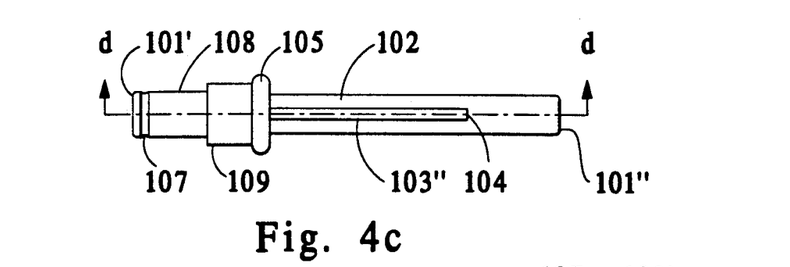
FIG. 4c is a side view of the needle cap of FIG. 4a with the needle cap rotated 90° about its lengthwise axis.
Figure 4D:
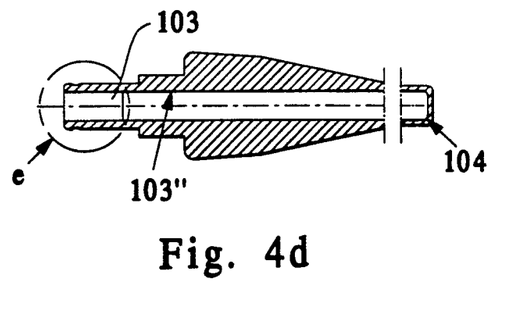
FIG. 4d is a side cross-sectional view of the needle cap taken along line d—d in FIG. 4c.
Figure 4E:
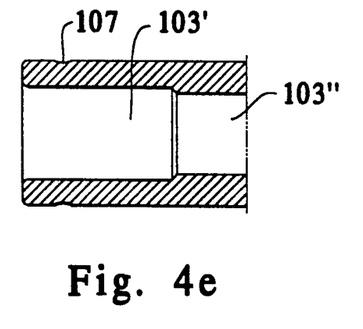
FIG. 4e is a detailed view of the portion e of FIGS. 4a and 4d.

As shown in FIG. 3c, the hypodermic needle 2 is pointed at both the end proximal to the user 2' and the end distal to the user 2'. The syringe is activated for use by moving needle hub 3 toward the membrane 42 so that the proximal pointed end 2' of the needle 2 penetrates membrane 42. The distal pointed end 2" of the needle is used to pierce the skin of a patient so that medicament can be administered intravenously or intramuscularly.

Figure 1A:
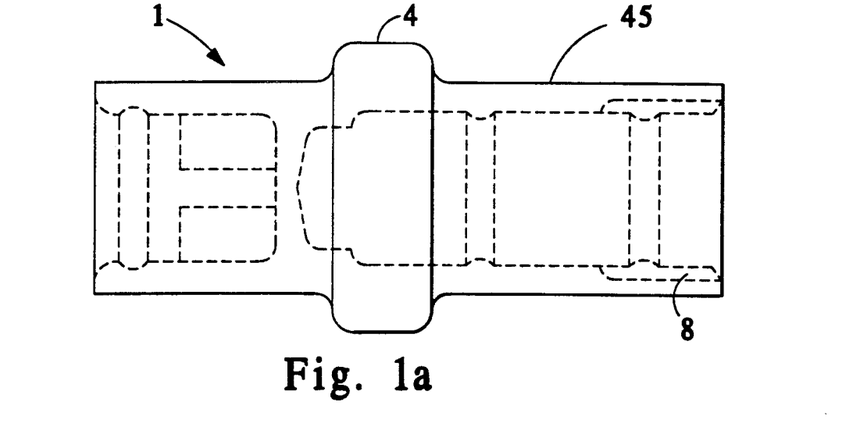
FIG. 1a is a side view of an injection port cylinder in accordance with one embodiment of the invention.
Figure 1B:
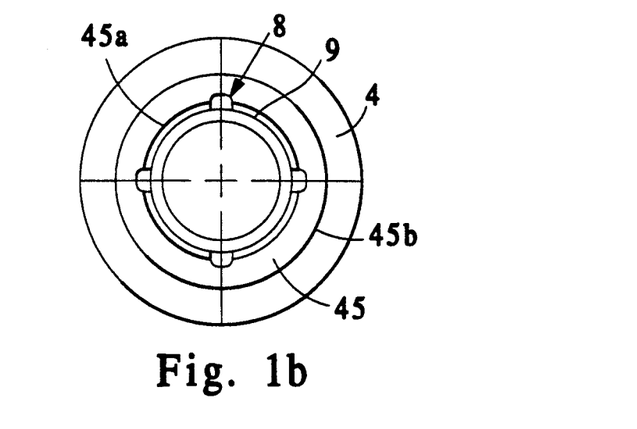

In the preferred embodiment of FIGS. 1a-1e, the injection port 1 includes vent means for preventing reuse of the Thomas syringe by refilling the reservoir with a Luer syringe. The vent means preferably include one or more longitudinal grooves 8 in the interior wall surrounding the elongated port cylinder chamber 12. More preferably, the vent means include two pairs of diametrically opposed grooves 8 as shown in FIG. 1b. When the tip of a Luer syringe is inserted into the grooved port cylinder 45, pressure from the Luer syringe is vented through the grooves 8. Thus, a Luer syringe cannot be effectively used to refill the reservoir of a Thomas syringe.

To further deter reuse, the preferred injection port 1 additionally includes one-way valve means for permitting fluid flow toward the distal end of the port but preventing substantial fluid flow in the opposite direction. In addition, the valve means allows aspiration as described hereinafter. The valve means include a valve seat 5 inserted at the proximal end of valve chamber 11, which is retained in place by a circumferential lip or rib (or bead) 52 mating with a circumferential depression 49 in the interior wall surface 45a. A number of discrete ribs 7 are attached radially to inside wall 45a on their outer side and to membrane 42 at their distal end, thereby defining both a central cylindrical cavity 41a and a series of spaces 41b between the ribs 7. The proximal ends 7' of the ribs 7 define a flat plane and are suitably dimensioned to prevent valve 6 from entering cavity 41a. A diaphragm or valve flap 6 is positioned between valve seat 5 and ribs 7.

Figure 1C:
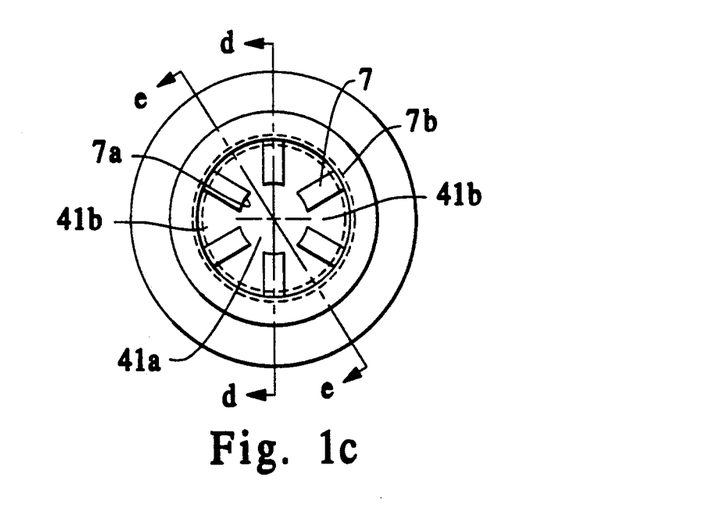
Figure 1D:
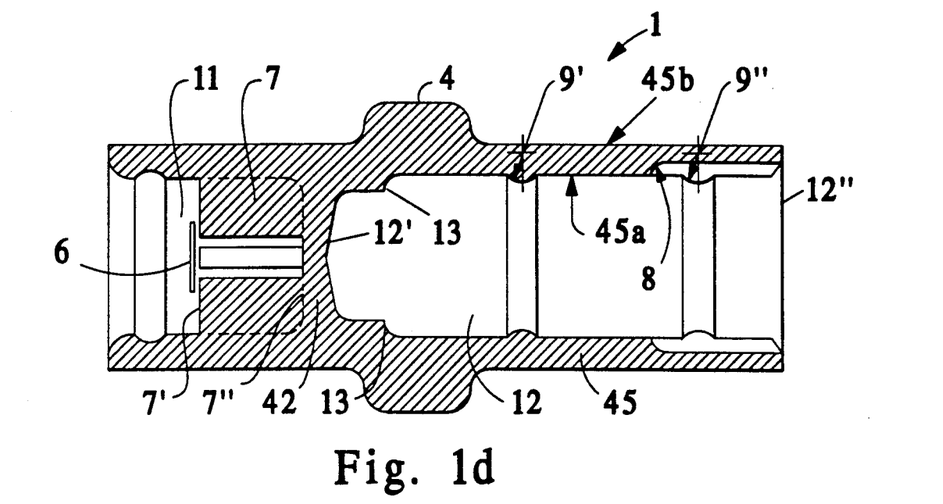
FIG. 1d is a side cross-sectional view of the injection port taken along line d—d in FIG. 1c.

In the preferred embodiment illustrated in FIG. 1c, six ribs 7 are provided. Each rib 7 has a side 7b connected to wall surface 45a and an opposite side 7a. Central-cavity 41a is defined by the area inside interior rib sides 7a. The distal base 7" of each rib 7 is connected to membrane 42.

Preferably, the valve 6 is circular and free-floating with a diameter large enough for the valve to cover the valve seat opening 55 while resting in contact with inside wall 45a to prevent refilling. The valve 6 has a diameter smaller than that defined by walls 45a in valve chamber 11 so that the medicament being injected can flow freely through some of the spaces 41b between the ribs 7 and thus into the central cavity 41a, even though valve 6 blocks the proximal end of the central cavity 41a. Preferably, the diameter of valve 6 is 125 mm, the internal diameter of valve chamber 11 is 160 mm, the space within which valve 6 moves (i.e., the distance between the plane defined by the proximal ends 7' of the ribs 7 and the distal end 54" of the valve seat 5) is 15 mm and valve flap 6 is 3 mm thick. The valve flap 6 may be hinged to valve seat 5.

Valve 6 may be made of plastic or metal such as stainless steel. For achieving the best seal of valve seat opening 55, valve 6 preferably is constructed of a plastic which under pressure will tend to conform to the distal surface 54" of valve seat 5. Polyethylene is a preferred material for valve 6. Other plastics having similar physical properties, such as polypropylene and appropriate grades of silicone and polyurethanes, may be used.

Figure 2A:
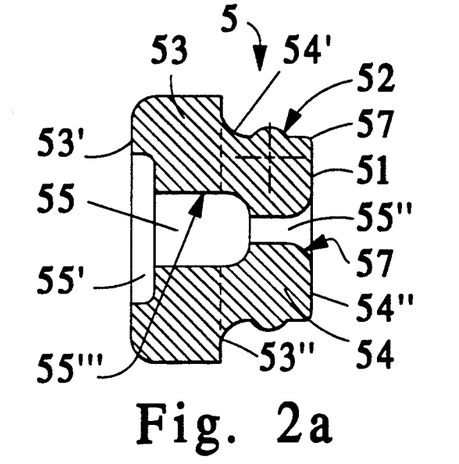
FIG. 2a is a side cross-sectional view of a preferred valve seat according to the invention.
Figure 2B:
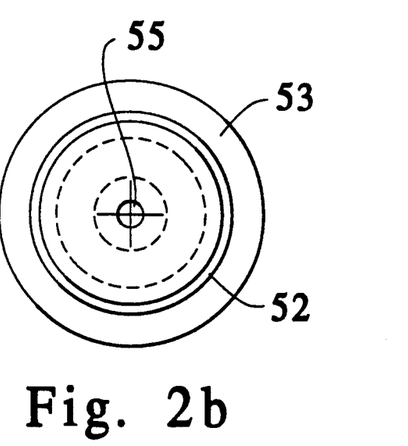

FIGS. 2a and 2b depict a preferred embodiment of valve seat 5. The seat 5 preferably has a cylindrical neck portion 54 and a larger cylindrical flange portion 53. Neck 54 has a distal neck end 54" and a proximal neck end 54'. Flange 53 has a proximal flange end 53' and a distal flange end 53". The flange 53 is dimensioned to preferably have substantially the same outer diameter as the valve chamber 11 of the port cylinder 45. The outer diameter of neck 54 is dimensioned to fit within the interior surface of valve chamber 11.

Preferably valve seat 5 is made of a resilient plastic material, such as polyethylene, and a circumferential bead 52 is provided on the outer surface of neck 54 which mates with a bead groove 49 in valve chamber 11 in a sealed snap-fit thereby securely connecting valve seat 5 to the port cylinder 45.

The distal end 54" of the neck 54 provides a valve seat surface 51, which preferably is smooth. The distal end 54" preferably has rounded edges 57 around its inner and outer circumference.

The valve seat surface 51 has a central opening 55 which has a smaller diameter than valve flap 6 as described above. Opening 55 extends from the distal end 54" to the proximal end 53, of valve seat 5, thereby operatively connecting the injection port assembly 1 to the syringe reservoir which, in this preferred embodiment is a collapsible or oil-can type reservoir means 102 (see FIG. 5) of a Thomas syringe. The diameter of the proximal end 55' of opening 55 is preferably greater than the diameter of its distal end 55", with a central portion 55''' having a diameter therebetween. When the seat 5 is in place on the port cylinder 45, opening 55 axially aligns with valve chamber 11.

Figure 5:
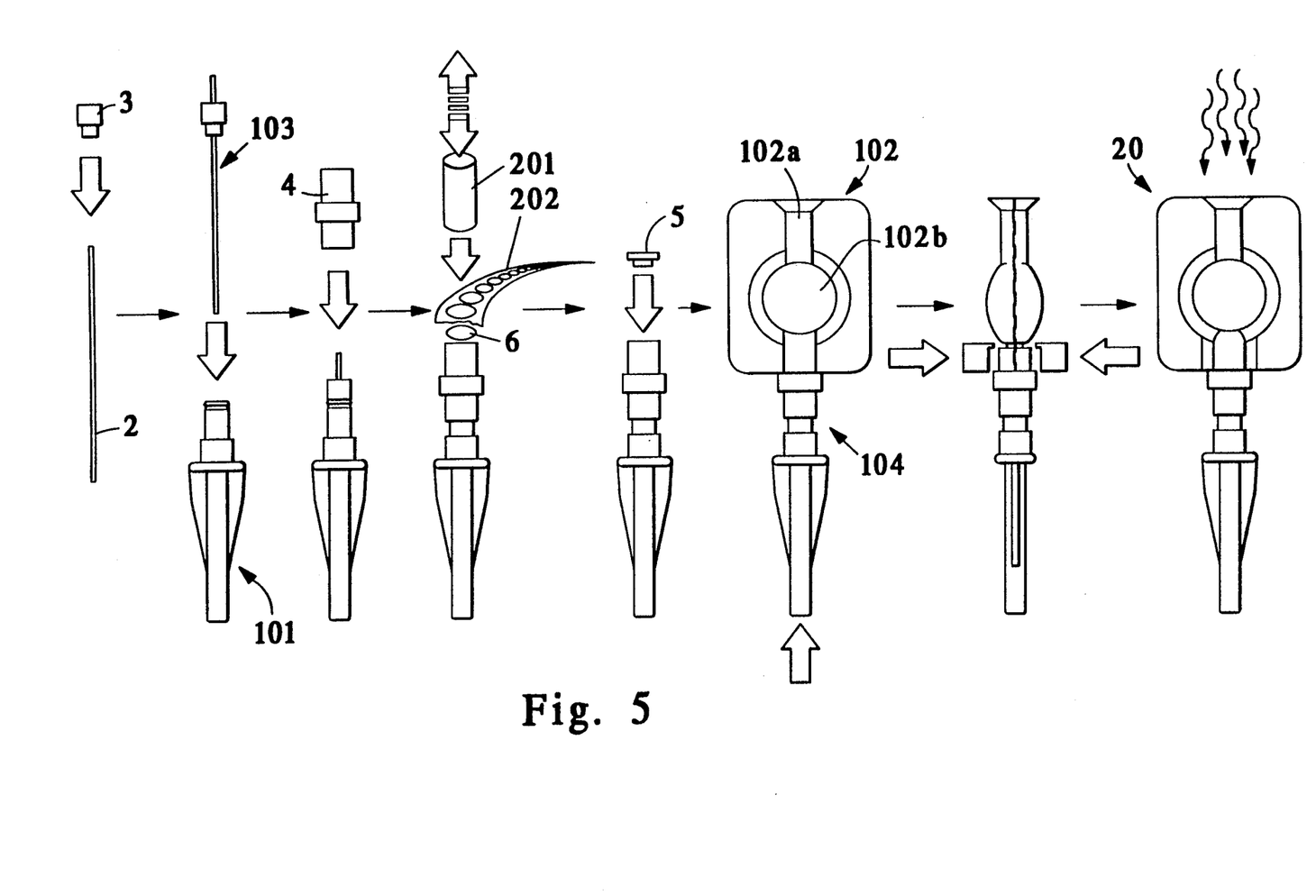
FIG. 5 is a flow diagram schematically illustrating a preferred method of manufacturing a single-use syringe having the injection port in accordance with the present invention.

Preferably, the valve seat 5 embodiment of FIG. 2 is used with the port cylinder 45 embodiment shown in FIGS. 1a–1e. The port cylinder wall 45 has a distal port opening 43 for operatively connecting to a needle assembly 103 and a protector cap 101 as shown in FIG. 5.

FIG. 3c shows the needle assembly 103 which comprises a hub 3 with hypodermic needle 2 secured along the center line of the hub 3. As shown in FIGS. 3a and 3b, the hub 3 has a main body 31 at the proximal end and a hub neck 32 at the distal end. A central cavity 33 runs through the axial length of the hub 3. The central cavity 33 has a proximal portion 33, within the main body 31 and a distal portion 33" within the hub neck 32. The distal cavity portion 33" is slightly larger than the diameter of the hypodermic needle 2, while the proximal cavity portion 33' is significantly larger in diameter to accommodate the adhesive which secures the needle 2 to the hub 3. In the embodiment shown, the proximal portion 33' of the cavity tapers down at 33''' to the distal portion 33". When the needle 2 is 23-gauge (24.5/25.5 mm diameter) stainless steel seamless tubing, a diameter of 26 mm for the distal portion 33" of the cavity provides ease of assembly and good support for needle 2, and a diameter of 93 mm for the proximal portion 33' of the cavity permits good adhesive application and bonding. Any medically acceptable adhesive which can bond stainless steel to the material of the hub 3 may be used. When polystyrene is used for the hub 3, a UV-curing epoxy resin is preferred.

Figure 1E:
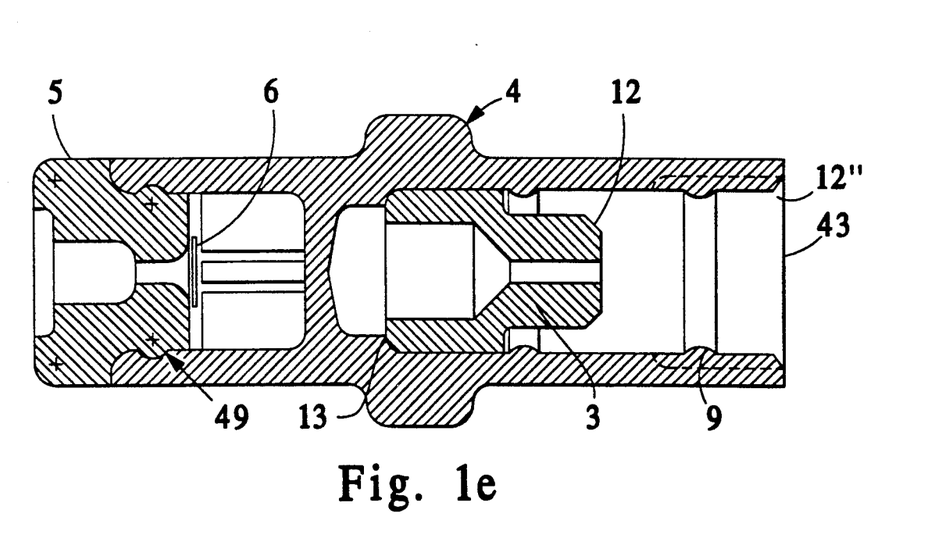
FIG. 1e is a side cross-sectional view of the injection port taken along line e—e in FIG. 1c, with the valve seat of FIG. 2a and the needle hub of FIG. 3a assembled therein.

For the port cylinder 45 shown in FIG. 1e, the distal end 12" of elongated chamber 12 has an internal diameter of 164 mm which tapers down toward a shoulder 13 near the proximal end 12' to an internal diameter of 156 mm just before the shoulder 13. The internal diameter at the shoulder 13 is 130 mm. Chamber 12 has two internal ribs 9 axially spaced apart for positioning the hub 3. The distal rib 9" reduces the internal diameter to 151 mm and the rib 9' reduces the internal diameter to 148 mm, with the distance between ribs 9' and 9" being 179 mm, and the distance from proximal rib 9' to the shoulder 13 being 134 mm. With these dimensions, the main hub body 31 has an outer diameter of 156 mm and a length of 119 mm, and the hub 3 has an overall length of 215 mm.

Port cylinder 45, as well as valve seat 5, may be constructed of any medical grade plastic which can be molded accurately and possesses sufficient resilience so that parts can easily be snap-fitted together to produce a secure assembly. When the syringe unit is aspirated after activation as discussed hereinafter, the blood will appear in valve chamber 11. Since the port 1 is molded as a unitary and integral part, the plastic used should have sufficient translucence so that the blood is easily visible. Polyethylene is the preferred material for the port cylinder 45, but polypropylene, silicone resins, and other materials having the aforementioned properties may be used.

The internal taper of chamber 12 assists in removing the port cylinder 45 from the mold, while the dimensions of the chamber 12, distal rib 9" and hub main body 31 permit ease of assembly while retaining the needle hub 3 securely in chamber 12 after assembly. Tighter (i.e., smaller tolerance between) dimensions of proximal rib 9' and the proximal chamber end 12' require firm pressure on hub 3 to activate the syringe and prevent accidental activation, and also assure accurate axial alignment of needle 2 so that during activation the needle 2 pierces membrane 42 to penetrate into cavity 41a. Shoulder 13 forms a stop to the hub main body 31, precisely regulating the depth of penetration of needle 2 into cavity 41a without any need for visual inspection.

The distal needle end 2" is preferably protected by a needle cap 101 shown in FIGS. 4a–4e. The cap 101 has a cylindrical main body 102 with a central cavity 103 running from the proximal end 101' to terminate in a wall 104 which closes the distal end 101". Intermediate the ends of cap 101 is a flange 105 with opposed fins 106 depending therefrom and tapering down toward the distal cap end 101". The dimensions of flange 105 and fins 106 are preferably selected to assist gripping by the fingers to urge the hub 3 toward the proximal chamber end 12' to activate the syringe; however, the dimensions are not critical. However, the proximal portion 103' of central cavity 103 must have a diameter to receive the neck 32 of hub 3. In the embodiment shown, the neck 32 has an outside diameter of 108 mm and the proximal cavity portion 103' has an internal diameter of 110 mm for a depth adequate to engage all of neck 32. The distal portion 103" of central cavity extending toward end wall 104 has a slight taper to facilitate removal from the mold.

The outer cap surface 101b has a circumferential channel 107 near the proximal end 101' to provide a snap-fit with distal rib 9" of chamber 12, thereby providing a secure unit after assembly. The outer diameter of the proximal cap end 101' (other than at channel 107) is slightly less than the internal diameter of chamber 12 to form a neck 108 for a distance from the proximal cap end 101', such that this distance plus the length of the main hub body 31 is equal to the distance from shoulder 13 of chamber 12 to the distal chamber end 12'. The neck 108 terminates in a shoulder 109 which has a diameter greater than the internal diameter of chamber 12. With this construction, shoulder 109 reinforces shoulder 13 to prevent excessive penetration of needle 2 into central cavity 41a after activation.

The operation of the valve means of the injection port 1 will now be described. The syringe is activated by holding the injection port 1 with medicament reservoir 102 thereon in one hand, preferably gripped at flange 4, and the cap 101 in the other hand, preferably gripped at flange 105 and fins 106, and firmly pressing the two units together until engagement of hub main body 31 with shoulder 13 of chamber 12 as shown in FIG. 1e and engagement of shoulder 109 of cap 101 with wall 45 prevent further lateral displacement. During this procedure needle 2 penetrates membrane 42 and forms a secure fluid connection with cavity 41a.

After removal of cap 101, needle 2 is then inserted in the patient and the syringe is aspirated by pushing lightly on the opposing faces of fluid reservoir 102b and then relaxing the pressure. If needle 2 is properly positioned in the patient, a small but easily visible amount of blood will be drawn up the needle 2 into cavity 41a and spaces 41b where it can be observed. Pressure is then reapplied to reservoir 102b causing the valve flap 6 to move toward ribs 7. The fluid is able to flow around the valve 6, through the passages 41b between radial ribs 7 into cavity 41a, into the proximal end 21 of the needle located in cavity 41a, and through the needle 2 into the patient. During injection, the position of the valve flap 6 in the valve chamber 11 is determined by principles of fluid mechanics. Thus, the dimensions and weight of the valve flap 6 are selected in view of factors such as the pressure exerted against the valve 6 by the fluid flowing around it.

When refilling of the syringe is attempted with the fluid flowing in the direction of reservoir 102b, the valve flap 6 is forced against valve seat surface 51. Thus, valve 6 blocks opening 55, so that fluid cannot enter the valve seat 5 and fluid connection with the reservoir 102 is obstructed.

As described above, the injection port 1 is preferably used with a Thomas-type system to provide an improved syringe 20 as shown in FIG. 5. The preferred method of manufacturing such a syringe 20 is schematically illustrated in FIG. 5.

The first step in the preferred manufacturing process is shown at the far left of FIG. 5. In the first step, a needle hub 3 is pressed onto needle 2 and glued in place to form a needle assembly 103.

Proceeding from left to right in FIG. 5, in the second step the needle assembly is dropped into a protector cap 101. The cap 101 may be formed from a molding of a rigid polymer, such as high density polyethylene. The length of the protector cap 101 is selected to preferably fit a ⅜-inch needle. Also, the cap flange 105 is located to provide optimal activation stability. During activation, the cap flange 105 allows the operator to more easily control lateral movement of the needle hub 3 within the port cylinder 45 by applying a force to the flange 105.

After the needle assembly 103 has been dropped into protector cap 101, the port cylinder 45 of the present invention is pressed onto the needle assembly. Preferably, the hub 3 is positioned between the pair of positioning lips 9.

In the fourth step shown in FIG. 5, a diaphragm or valve flap 6 is punched from a continuous strip 202 into valve chamber 11 of the port cylinder 45. A die 201 or similar means can be used to punch out each valve body 6 from the continuous strip 202. Preferably, the valve flaps 6 are punched from a strip of polyethylene. Alternatively, the valve flaps can be molded.

Next, the valve seat 5 is pressed into port cylinder 45 to form a port-needle assembly 110.

In the sixth step, the port-needle assembly 110 is located in a preformed reservoir means 102 preferably having a central reservoir portion 102b and a filling neck portion 102a or other means for filling the reservoir. Alternatively, the reservoir may be prefilled with a medicament. The manufacture of the reservoir means 102 is described in detail in U.S. Pat. No. 4,955,871.

The reservoir means 102 is then heat-sealed to the port-needle assembly 110 in the seventh step to form a syringe assembly 20.

The above steps may be repeated to mass-produce a number of syringes 20 at relatively low cost. Finally, in the last step shown at the right of FIG. 5, the syringe assemblies 20 may be sterilized, preferably by radiation, filled with medicament and sealed as described in U.S. Pat. No. 4,955,871.

The injection port assembly 1 can also be used as a separate unit for insertion at the distal end of the barrel of a conventional prefilled syringe to make the syringe non-reusable. In this application flange 4 is eliminated, elongated chamber 12 is replaced by extending central cavity 41a as described hereafter, the valve flap assembly is sized to fit the barrel of the syringe and comprises the valve chamber 11 (modified by extending central cavity 41a through membrane 42, which becomes the exterior and distal wall of chamber 12), valve flap 6 and valve seat 5.

Although specific embodiments of the injection port, syringe, and manufacturing thereof have been described, various modifications will be apparent to those skilled in the art. For example, various numbers, shapes and sizes for the radial ribs may be used. Thus, the scope of the present invention is not intended to be limited to the foregoing description but is defined by the claims appended hereto.

We claim:

1. An injection port assembly insertable at a distal end of a prefilled medicament reservoir of a medical syringe in order to make the syringe substantially non-reusable by permitting substantial fluid flow out of the distal end of the syringe medicament reservoir and preventing substantial fluid flow into said distal end of the syringe medicament reservoir, said injection port assembly comprising:

a tubular wall having a proximal wall portion and a distal wall portion; a valve chamber in the proximal wall portion for forming a fluid-tight seal with the syringe, said valve chamber having a proximal chamber end and a distal chamber end, said distal chamber end having a central aperture for communicating with a hypodermic needle; a plurality of radial ribs surrounding the central aperture and extending from the central aperture to the tubular wall and defining both a central cavity extending in a proximal direction and a series of passages between the ribs, the passages communicating with the central cavity, a valve seat closing the proximal chamber end and having a valve seat surface surrounding a central opening for connecting the valve chamber with said medicament reservoir; a valve flap disposed in the valve chamber between the valve seat and the ribs, said valve flap being free to move between the valve seat and the ribs as pressure is applied to the valve flap by fluid entering the valve chamber, the valve flap having a diameter smaller than the inner diameter of the chamber and large enough to sealingly cover the central opening when in contact with the tubular wall of the chamber and also large enough to cover the central cavity but not all of the passages between the ribs; and means for positioning the injection port assembly in a syringe between a medicament reservoir and a hypodermic needle.

2. A syringe device associated with a syringe and comprising an injection port associated with an outlet of a fluid reservoir of said syringe, said injection port comprising;

a port cylinder having a central axis, said port cylinder including a tubular wall having a proximal cylinder end, a distal cylinder end, an interior wall surface and an exterior wall surface; an elongated chamber defined within a distal portion of the interior wall surface, said elongated chamber having a proximal chamber end between said proximal cylinder end and said distal cylinder end; a valve chamber within a proximal portion of the interior wall surface for axially communicating with the proximal chamber end, said valve chamber having a proximal valve chamber portion and a distal valve chamber portion; a circular membrane connected to the interior wall surface and extending between said valve chamber and said elongated chamber; a plurality of radial ribs extending between said membrane and said valve chamber, said radial ribs defining a central cavity extending along the central axis and a radial passage between each of the ribs;

a valve seat connected to the proximal cylinder end, said valve seat including a valve neck portion having an exterior neck surface fitting within the interior wall surface and having a distal neck end and a proximal neck end, said valve neck portion including an interior neck surface defining a central neck opening axially communicating with said valve chamber, and a valve seat surface at the distal neck end having an inner diameter defining said central neck opening, said valve seat surface having an outer diameter smaller than the diameter of the interior wall surface, said valve seat further including a valve flange portion having a distal flange end and a proximal flange end, said distal flange end connected to the proximal neck end, said valve flange portion having a central flange opening therethrough axially communicating with said central neck opening; and a valve flap disposed in said valve chamber, said valve flap having a diameter greater than the diameter of the central cavity between the radial ribs and greater than the diameter of said central neck opening, said valve flap being operable when a needle is inserted through the membrane for allowing substantial fluid flow from the valve chamber into the needle and through the needle in a direction along the central axis toward the distal end of the tubular wall, and for preventing substantial fluid flow opposite to said direction.

3. A syringe device as recited in claim 2, wherein said valve flap is made of plastic.

4. A syringe device as recited in claim 2, wherein said valve flap is made of metal.

5. A syringe device as recited in claim 2, wherein said radial ribs include six ribs each having a side connected to the interior wall surface and a rib base connected to said membrane.

6. A syringe device as recited in claim 2, wherein said interior wall surface has a circumferential bead groove near the proximal wall end, and the exterior neck surface of the valve seat has a circumferential bead thereon which fits within said circumferential bead groove.

7. A syringe device as recited in claim 2, wherein said port cylinder further includes a flange on the exterior wall surface at an axial location between said distal cylinder end and said proximal cylinder end.

8. A syringe device as recited in claim 2, wherein the interior wall surface around said elongated chamber has a pair of circumferential ribs axially spaced apart for positioning a needle hub therebetween.

9. A syringe device as recited in claim 2, wherein said port cylinder further includes vent means for venting said elongated chamber.

10. A syringe device as recited in claim 9, wherein said vent means include at least one longitudinal groove on the interior wall surface extending from said distal cylinder end toward said proximal chamber end.

11. A syringe device as recited in claim 9, further comprising a needle axially supported in a needle hub held in said elongated chamber, said needle hub having an outer diameter slightly less than the diameter of the interior wall surface.

12. A syringe device as recited in claim 2, further comprising a needle axially supported in a needle hub held in said elongated chamber, said needle hub having an outer diameter slightly less than the diameter of the interior wall surface.

13. A syringe device as recited in claim 12, further comprising said reservoir connected to the proximal end of said port cylinder and fluidly communicating with said central neck opening.

14. A syringe device as recited in claim 13, further comprising a protector cap connected to the distal cylinder end.

15. A syringe device as recited in claim 13, wherein said reservoir includes a compressible oil-can type reservoir.

16. A syringe device as recited in claim 15, wherein the reservoir is heat-sealed to said injection port.

17. A syringe device operatively associatable with a syringe and comprising an injection port operatively associatable with an outlet of a fluid reservoir of said syringe, said injection port comprising:
   a port cylinder having a central axis, said port cylinder including a tubular wall having a proximal wall end surrounding a proximal cylinder opening, a distal wall end surrounding a distal cylinder opening, an interior wall surface and an exterior wall surface; an elongated chamber defined within a distal portion of the interior wall surface; a circular membrane circumferentially connected to the interior wall surface between said distal wall end and said proximal wall end; and vent means for venting pressure introduced into said elongated chamber from a distal end of said port cylinder during attempts to refill a reservoir from said distal end when said reservoir is operatively attached to a proximal end of said port cylinder; and
   one-way valve means operatively associated with said injection port and operable when a needle is inserted through the membrane for allowing substantial fluid flow from the proximal cylinder opening into the needle and through the needle in a direction along the central axis toward the distal wall end, and for preventing substantial fluid flow opposite to said direction.

18. A syringe device operatively associatable with a syringe and comprising an injection port operatively associatable with an outlet of a fluid reservoir of said syringe, said injection port comprising:
   a port cylinder having a central axis, said port cylinder including a tubular wall having a proximal wall end surrounding a proximal cylinder opening, a distal wall end surrounding a distal cylinder opening, an interior wall surface and an exterior wall surface; an elongated chamber defined within a distal portion of the interior wall surface; a circular membrane circumferentially connected to the interior wall surface between said distal wall end and said proximal wall end; and vent means for venting pressure introduced into said elongated chamber from a distal end of said port cylinder during attempts to refill a reservoir from said distal end when said reservoir is operatively attached to a proximal end of said port cylinder, said vent means comprising one or more pairs of diametrically opposed longitudinal grooves running lengthwise along the interior wall surface of said elongated chamber;
   a valve chamber within a proximal portion of the interior wall surface between said proximal wall end and said membrane and axially communicating with the proximal cylinder opening; a plurality of radial ribs extending between said membrane and said valve chamber, said radial ribs defining a central cavity extending along the central axis and a radial passage between each adjacent rib;
   a valve seat connected to the proximal cylinder end, said valve seat including a valve neck portion having an exterior neck surface fitting within the interior wall surface and having a distal neck end and a proximal neck end, said valve neck portion including an interior neck surface defining a central neck opening axially communicating with said valve chamber, and a valve seat surface at the distal neck end having an inner diameter defining said central neck opening, said valve seat surface having an outer diameter smaller than the diameter of the interior wall surface, said valve seat further including a valve flange portion having a distal flange end and a proximal flange end, said distal flange end connected to the proximal neck end, said valve flange portion having a central flange opening therethrough axially communicating with said central neck opening; and
   a valve flap disposed in said valve chamber, said valve flap having a diameter greater than the diameter of the central cavity between the radial ribs and greater than the diameter of said central neck opening, said valve flap being operable when a needle is inserted through the membrane for allowing substantial fluid flow from the valve chamber into the needle and through the needle in a direction along the central axis toward the distal wall end, and for preventing substantial fluid flow opposite to said direction, said valve flap being movable in said valve chamber.

* * * * *